United States Patent
Yap et al.

(10) Patent No.: US 7,520,871 B2
(45) Date of Patent: Apr. 21, 2009

(54) SYSTEM AND METHOD FOR TENSION-ACTIVATED FLUID CONTROL

(75) Inventors: Marc Yap, Millville, UT (US); James Doheny Bruke, Encinitas, CA (US); Sean B. Cahill, Temecula, CA (US); Elizabeth A. Paderi, Chesler, NY (US); Ryan Sells, San Diego, CA (US); David W. Meibos, West Jordan, UT (US)

(73) Assignee: LMA North America, Inc, San Diego, CA (US)

( * ) Notice: Subject to any disclaimer, the term of this patent is extended or adjusted under 35 U.S.C. 154(b) by 174 days.

(21) Appl. No.: 10/946,269

(22) Filed: Sep. 21, 2004

(65) Prior Publication Data

US 2007/0078380 A1  Apr. 5, 2007

Related U.S. Application Data

(63) Continuation-in-part of application No. 10/218,106, filed on Aug. 12, 2002, now Pat. No. 6,893,414, and a continuation-in-part of application No. 10/909,157, filed on Jul. 30, 2004, and a continuation-in-part of application No. 10/903,951, filed on Jul. 30, 2004, now Pat. No. 7,462,163.

(51) Int. Cl.
*A61M 5/00* (2006.01)
*F16K 31/00* (2006.01)
*A61M 37/00* (2006.01)

(52) U.S. Cl. .................. 604/249; 604/131; 251/349
(58) Field of Classification Search ............... 604/131, 604/132, 133, 247, 30, 249; 137/512.15, 137/853; 251/349, 354
See application file for complete search history.

(56) References Cited

U.S. PATENT DOCUMENTS

| | | | |
|---|---|---|---|
| 2,859,932 A | * | 11/1958 | Mackal .................. 251/349 |
| 3,920,014 A | | 11/1975 | Banko |
| 4,070,725 A | | 1/1978 | Austin et al. |
| 4,177,810 A | | 12/1979 | Gourlandt |

(Continued)

FOREIGN PATENT DOCUMENTS

EP  1430924 A1  6/2004

(Continued)

*Primary Examiner*—Kevin C Sirmons
*Assistant Examiner*—Elizabeth R MacNeill
(74) *Attorney, Agent, or Firm*—David W. Meibors; Barbara Daniels; Daniel F. Justin (57) ABSTRACT

A medication infusion system may include a controller and a reservoir module including a reservoir containing medication to be delivered to an internal wound site via the controller. The controller may have a peristaltic pump driven by a motor to urge medication to flow toward the internal wound site, through a conduit. When the conduit is not tensioned via engagement with the pump, a valve blocks fluid flow to prevent unrestricted flow of medication. The valve may have a tapered plunger separated from an annular valve seat by a portion of the conduit that elongates under tension to enable withdrawal of the plunger from the valve seat. Alternatively, the valve may have features such as a spherical plunger between two annular valve seats, a rigid tubular member biased with respect to the conduit, or an opening in the conduit that moves axially or radially to enable fluid flow.

36 Claims, 7 Drawing Sheets

U.S. PATENT DOCUMENTS

| | | | |
|---|---|---|---|
| 4,180,067 A | 12/1979 | Derlien | |
| 4,180,074 A | 12/1979 | Murry et al. | |
| 4,193,397 A | 3/1980 | Tucker et al. | |
| 4,217,894 A | 8/1980 | Franetzki | |
| 4,231,287 A | 11/1980 | Smiley | |
| 4,244,365 A | 1/1981 | McGill et al. | |
| 4,258,711 A | 3/1981 | Tucker et al. | |
| 4,273,121 A | 6/1981 | Jassawalla | |
| 4,276,004 A | 6/1981 | Hahn | |
| 4,277,226 A | 7/1981 | Archibald | |
| 4,278,085 A | 7/1981 | Shim | |
| 4,300,554 A | 11/1981 | Hessberg et al. | |
| 4,308,866 A | 1/1982 | Jelliffe et al. | |
| 4,324,243 A * | 4/1982 | Helfgott et al. | 604/541 |
| 4,332,246 A | 6/1982 | Thomson | |
| 4,335,835 A | 6/1982 | Beigler et al. | |
| 4,355,638 A | 10/1982 | Iwatschenko et al. | |
| 4,369,780 A | 1/1983 | Sakai | |
| 4,395,259 A | 7/1983 | Prestele et al. | |
| 4,396,385 A | 8/1983 | Kelly et al. | |
| 4,398,910 A | 8/1983 | Blake et al. | |
| 4,468,216 A | 8/1984 | Muto | |
| 4,469,481 A | 9/1984 | Kobayashi | |
| 4,479,797 A | 10/1984 | Kobayashi et al. | |
| 4,496,343 A | 1/1985 | Prosl et al. | |
| 4,519,792 A | 5/1985 | Dawe | |
| 4,525,164 A | 6/1985 | Loeb et al. | |
| 4,527,588 A * | 7/1985 | Tseo et al. | 251/349 |
| 4,559,045 A | 12/1985 | Danby et al. | |
| 4,563,179 A | 1/1986 | Sakai | |
| 4,604,090 A | 8/1986 | Reinicke | |
| 4,619,643 A | 10/1986 | Bai | |
| 4,623,329 A | 11/1986 | Drobish et al. | |
| 4,648,872 A | 3/1987 | Kamen | |
| 4,650,469 A | 3/1987 | Berg et al. | |
| 4,652,260 A | 3/1987 | Fenton, Jr. et al. | |
| 4,653,987 A | 3/1987 | Tsuji et al. | |
| 4,657,486 A | 4/1987 | Stempfle et al. | |
| 4,657,490 A | 4/1987 | Abbott | |
| 4,668,220 A | 5/1987 | Hawrylenko | |
| 4,681,563 A | 7/1987 | Deckert et al. | |
| 4,681,566 A | 7/1987 | Fenton, Jr. et al. | |
| 4,687,475 A | 8/1987 | Tai et al. | |
| 4,692,141 A | 9/1987 | Mahurkar | |
| 4,692,153 A | 9/1987 | Berlin et al. | |
| 4,696,671 A | 9/1987 | Epstein et al. | |
| 4,706,368 A | 11/1987 | Crissman, III et al. | |
| 4,710,166 A | 12/1987 | Thompson et al. | |
| 4,756,706 A | 7/1988 | Kerns et al. | |
| 4,762,518 A | 8/1988 | Kreinick | |
| 4,795,439 A | 1/1989 | Guest | |
| 4,798,590 A | 1/1989 | O'Leary et al. | |
| 4,802,885 A | 2/1989 | Weeks et al. | |
| 4,813,937 A | 3/1989 | Vaillancourt | |
| 4,828,545 A | 5/1989 | Epstein et al. | |
| 4,840,542 A | 6/1989 | Abbott | |
| 4,840,620 A | 6/1989 | Kobayashi et al. | |
| 4,846,637 A | 7/1989 | Alderson et al. | |
| 4,882,575 A | 11/1989 | Kawahara | |
| 4,900,305 A | 2/1990 | Smith et al. | |
| 4,935,010 A | 6/1990 | Cox et al. | |
| 4,958,803 A * | 9/1990 | Chappell | 251/349 |
| 4,966,585 A | 10/1990 | Gangemi | |
| 4,976,590 A | 12/1990 | Baldwin | |
| 4,978,335 A | 12/1990 | Arthur, III | |
| 5,004,455 A | 4/1991 | Greenwood et al. | |
| 5,017,059 A | 5/1991 | Davis | |
| 5,019,047 A | 5/1991 | Kriesel | |
| 5,024,663 A | 6/1991 | Yum | |
| 5,045,075 A | 9/1991 | Ersek | |
| 5,046,486 A | 9/1991 | Grulke et al. | |
| 5,053,023 A | 10/1991 | Martin | |
| 5,059,174 A | 10/1991 | Vaillancourt | |
| 5,073,164 A | 12/1991 | Hollister et al. | |
| 5,078,683 A | 1/1992 | Sancoff et al. | |
| 5,098,380 A | 3/1992 | Aizawa et al. | |
| 5,098,387 A | 3/1992 | Wiest et al. | |
| 5,103,211 A | 4/1992 | Daoud et al. | |
| 5,106,374 A | 4/1992 | Apperson et al. | |
| 5,116,203 A | 5/1992 | Natwick et al. | |
| 5,116,310 A | 5/1992 | Seder et al. | |
| 5,135,498 A | 8/1992 | Kam et al. | |
| 5,167,623 A | 12/1992 | Cianci et al. | |
| 5,169,389 A | 12/1992 | Kriesel | |
| 5,178,609 A | 1/1993 | Ishikawa | |
| 5,180,365 A | 1/1993 | Ensminger et al. | |
| 5,188,603 A | 2/1993 | Vaillancourt | |
| 5,207,642 A | 5/1993 | Orkin et al. | |
| 5,242,407 A | 9/1993 | Struble et al. | |
| 5,244,463 A | 9/1993 | Cordner, Jr. et al. | |
| 5,246,347 A | 9/1993 | Davis | |
| 5,260,665 A | 11/1993 | Goldberg et al. | |
| 5,279,568 A | 1/1994 | Cater | |
| 5,399,166 A | 3/1995 | Laing | |
| 5,431,634 A | 7/1995 | Brown | |
| 5,433,704 A | 7/1995 | Ross et al. | |
| 5,451,215 A | 9/1995 | Wolter | |
| 5,464,392 A | 11/1995 | Epstein et al. | |
| 5,472,317 A | 12/1995 | Field et al. | |
| 5,472,420 A | 12/1995 | Campbell | |
| 5,480,380 A | 1/1996 | Martin | |
| 5,480,386 A | 1/1996 | Brohy et al. | |
| 5,483,222 A | 1/1996 | Tice | |
| 5,501,665 A | 3/1996 | Jhuboo et al. | |
| 5,503,538 A | 4/1996 | Wiernicki et al. | |
| 5,514,103 A | 5/1996 | Srisathapat et al. | |
| 5,522,803 A | 6/1996 | Teissen-Simony | |
| 5,547,472 A | 8/1996 | Onishi et al. | |
| 5,554,114 A | 9/1996 | Wallace et al. | |
| 5,584,811 A | 12/1996 | Ross et al. | |
| 5,616,121 A | 4/1997 | McKay | |
| 5,647,853 A | 7/1997 | Feldmann et al. | |
| 5,657,000 A | 8/1997 | Ellingboe | |
| 5,658,252 A | 8/1997 | Johnson | |
| 5,672,167 A | 9/1997 | Athayde et al. | |
| 5,681,283 A | 10/1997 | Brownfield | |
| 5,695,464 A | 12/1997 | Viallet | |
| 5,695,473 A | 12/1997 | Olsen | |
| 5,718,692 A | 2/1998 | Schon et al. | |
| 5,720,721 A | 2/1998 | Dumas et al. | |
| 5,728,069 A | 3/1998 | Montevecchi et al. | |
| 5,738,659 A | 4/1998 | Neer et al. | |
| 5,743,878 A | 4/1998 | Ross et al. | |
| 5,746,717 A | 5/1998 | Aigner | |
| 5,746,719 A | 5/1998 | Farra et al. | |
| 5,749,854 A | 5/1998 | Shen | |
| 5,755,691 A | 5/1998 | Hilborne | |
| 5,755,692 A | 5/1998 | Manicom | |
| 5,769,824 A | 6/1998 | Hjertman et al. | |
| 5,776,104 A | 7/1998 | Guignard et al. | |
| 5,782,805 A | 7/1998 | Meinzer et al. | |
| 5,791,880 A | 8/1998 | Wilson | |
| 5,795,326 A | 8/1998 | Siman | |
| 5,797,869 A | 8/1998 | Martin et al. | |
| 5,797,881 A | 8/1998 | Gadot | |
| 5,807,322 A | 9/1998 | Lindsey et al. | |
| 5,817,052 A | 10/1998 | Johnson et al. | |
| 5,826,621 A * | 10/1998 | Jemmott | 137/853 |
| 5,827,223 A | 10/1998 | Butterfield | |
| 5,891,101 A | 4/1999 | Wilcox et al. | |
| 5,904,666 A | 5/1999 | DeDecker et al. | |
| 5,906,589 A | 5/1999 | Gordon et al. | |
| 5,916,165 A | 6/1999 | Duchon et al. | |
| 5,935,106 A | 8/1999 | Olsen | |

| | | | | | | |
|---|---|---|---|---|---|---|
| 5,938,638 A | 8/1999 | Passariello et al. | | 6,248,093 B1 | 6/2001 | Moberg |
| 5,947,928 A | 9/1999 | Muller | | 6,248,100 B1 | 6/2001 | de Toledo et al. |
| 5,947,953 A | 9/1999 | Ash et al. | | 6,264,624 B1 | 7/2001 | Desmond, III et al. |
| 5,954,696 A | 9/1999 | Ryan | | 6,270,478 B1 | 8/2001 | Mern.o slashed.e |
| 5,957,889 A | 9/1999 | Poulsen et al. | | 6,270,490 B1 | 8/2001 | Hahnen |
| 5,957,890 A | 9/1999 | Mann et al. | | 6,280,399 B1 | 8/2001 | Rossin et al. |
| 5,961,485 A | 10/1999 | Martin | | 6,290,690 B1 | 9/2001 | Huculak et al. |
| 5,968,009 A | 10/1999 | Siman | | 6,299,598 B1 | 10/2001 | Bander |
| 5,968,014 A | 10/1999 | Neftel et al. | | 6,299,601 B1 | 10/2001 | Hjertman |
| 5,976,103 A | 11/1999 | Martin | | 6,302,864 B1 | 10/2001 | Nowosielski |
| 5,976,109 A | 11/1999 | Heruth | | 6,312,227 B1 | 11/2001 | Davis |
| 5,989,206 A | 11/1999 | Prosl et al. | | 6,319,222 B1 | 11/2001 | Andrew et al. |
| 5,989,222 A | 11/1999 | Cole et al. | | 6,325,788 B1 | 12/2001 | McKay |
| 6,001,079 A | 12/1999 | Pourchez | | 6,348,043 B1 | 2/2002 | Hagen et al. |
| 6,007,518 A | 12/1999 | Kriesel et al. | | 6,358,225 B1 | 3/2002 | Butterfield |
| 6,048,328 A | 4/2000 | Haller et al. | | 6,423,029 B1 | 7/2002 | Elsberry |
| 6,056,718 A | 5/2000 | Funderburk et al. | | 6,494,864 B1 * | 12/2002 | Kerwin et al. ............ 604/131 |
| 6,059,767 A | 5/2000 | Noriega | | 6,659,976 B2 * | 12/2003 | Beck et al. ............... 604/67 |
| 6,086,575 A | 7/2000 | Mejslov | | 6,742,992 B2 | 6/2004 | Davis |
| 6,113,574 A | 9/2000 | Spinello | | 2001/0025168 A1 | 9/2001 | Gross et al. |
| 6,132,415 A | 10/2000 | Finch et al. | | 2001/0056259 A1 | 12/2001 | Skinkle et al. |
| 6,149,621 A | 11/2000 | Makihara | | 2002/0016570 A1 | 2/2002 | Cartledge |
| 6,190,349 B1 | 2/2001 | Ash et al. | | 2002/0019612 A1 | 2/2002 | Watanabe et al. |
| 6,190,359 B1 | 2/2001 | Heruth | | | | |
| 6,193,704 B1 | 2/2001 | Winters | | | FOREIGN PATENT DOCUMENTS | |
| 6,200,292 B1 | 3/2001 | French et al. | | EP | 1073494 B1 | 7/2004 |
| 6,206,849 B1 | 3/2001 | Martin et al. | | WO | WO2004058334 A1 | 7/2004 |
| 6,210,361 B1 | 4/2001 | Kamen et al. | | WO | WO2004058337 A1 | 7/2004 |
| 6,217,556 B1 | 4/2001 | Ellingson et al. | | | | |
| 6,224,578 B1 * | 5/2001 | Davis et al. ............ 604/247 | | * cited by examiner | | |

SYSTEM AND METHOD FOR TENSION-ACTIVATED FLUID CONTROL

CROSS-REFERENCE TO RELATED APPLICATIONS

This application is a continuation-in-part of U.S. application Ser. No. 10/218,106, filed Aug. 12, 2002 now U.S. Pat. No. 6,893,414 and entitled INTEGRATED INFUSION AND ASPIRATION SYSTEM AND METHOD, U.S. application Ser. No. 10/909,157, filed Jul. 30, 2004 and entitled MEDICATION INFUSION SYSTEM AND METHOD, and U.S. application Ser. No. 10/903,951, filed Jul. 30, 2004 now U.S. Pat. No. 7,462,163 and entitled SYSTEM AND METHOD FOR BLOCKAGE DETECTION FOR MEDICATION INFUSION, the disclosures of which are incorporated herein by reference.

BACKGROUND OF THE INVENTION

1. The Field of the Invention

The present invention relates generally to the post-surgical treatment of closed wounds and specifically to methods and systems for infusion of a wound site to manage pain, swelling, bleeding and infection.

2. The Relevant Technology

One of the most difficult aspects of enduring a major surgical procedure is coping with the post-operative pain and swelling. Commonly, opioid analgesics, sometimes referred to as narcotics, are administered post-operatively to counter the pain associated with wound healing and recovery. However, the use of systemic opioid analgesics, whether administered by oral, intramuscular, or intravenous methods, includes a host of possible undesirable side effects, including: respiratory depression, renal function depression, nausea, constipation, ataxia, confusion, sweating, and itching. The length of hospital stay for patients undergoing a major surgical procedure is, in part, determined by the need to monitor and control the side effects of systemically administered opioid analgesics.

More recently, infusion pumps have been used to percutaneously deliver local anesthetics directly to the surgical wound. Thus, many of the undesirable side effects of systemic opioid analgesics are avoided. Furthermore, medication dosage is considerably less than systemic delivery since the medication is delivered directly to the affected site. However, contemporary percutaneous pain medication infusion pumps do not provide consistent relief of pain. Furthermore, many currently available medication infusion pumping arrangements are unable to adequately aspirate the affected site to reduce fluid build-up and swelling.

Yet further, many medication infusion pumps lack adequate safety measures to ensure that the proper dosage of medication is delivered. Some medication infusion pumps have safety measures that are too complex, and therefore cannot be reliably implemented, or that add unduly to the cost of the medication pump. Accordingly, existing medication infusion pumps may not be as cost-effective, failsafe, or easy to use as may be desirable. For controllers utilizing peristaltic pump technology, there may exist a unique need to ensure that the conduit through which the fluid is driven is properly tensioned before fluid flow is permitted, so that only the desired amount of medication is able to flow through the conduit when the pump is operating. Additionally, it is necessary to prevent unregulated flow through the conduit before the conduit is tensioned about the peristaltic pump.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
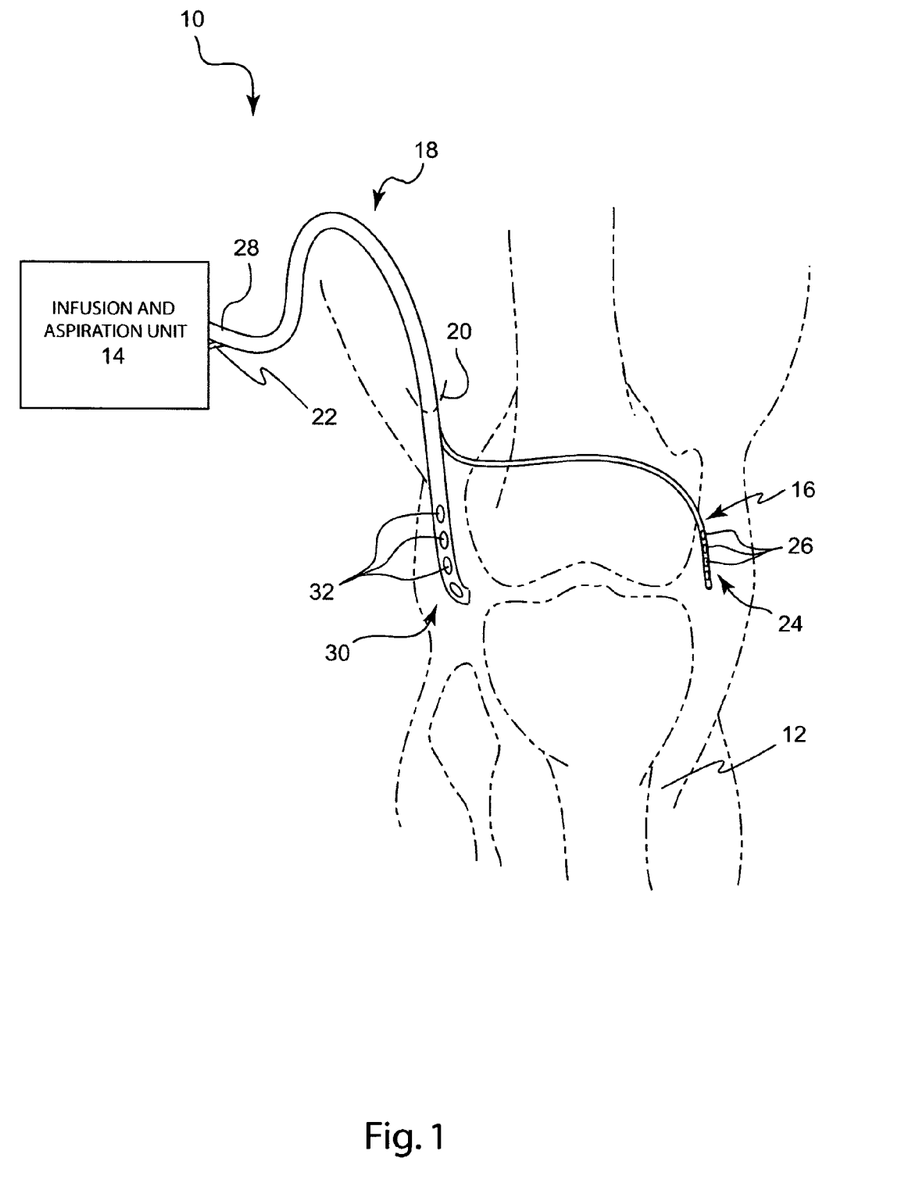
FIG. 1 is a schematic view of an integrated infusion and aspiration system applied to the knee of a patient.

Referring to FIG. 1, a schematic view illustrates an integrated infusion and aspiration system 10, or system 10, according to one embodiment of the invention. The system 10 may be postoperatively used to provide pain relief medication directly to an internal wound site 12. In FIG. 1, the internal wound site 12 is a knee that has been surgically treated, for example, via a partial or total knee arthroplasty. However, the systems and methods of the present invention are not limited to postoperative use, and may be used to relieve pain before or after treatment of injury to any part of the body. In addition to providing pain relief medication to the internal wound site 12, the system 10 aspirates internal fluids, such as spent medication and biological fluids, from the internal wound site 12.

In the embodiment of FIG. 1, the system 10 includes an integrated infusion and aspiration unit 14, hereinafter referred to as an infusion unit 14, that provides pressurized medication and provides a corresponding relative vacuum to receive fluids aspirated from the internal wound site 12. Additionally, the system 10 includes an infusion catheter 16 through which medication is delivered to the internal wound site 12, and an aspiration catheter 18 through which fluids are received in the infusion unit 14 from the internal wound site 12. As shown, a portion of the infusion catheter 16 may be nested within a corresponding portion of the aspiration catheter 18 so that both catheters 16, 18 gain access to the internal wound site 12 through a single point-of-entry 20.

As illustrated, the infusion catheter 16 has a proximal end 22 and a distal end 24, with a plurality of flow orifices 26 arrayed along the distal end 24 to provide infusion of medication along a relatively broad dispersal path within the internal wound site 12. Similarly, the aspiration catheter 18 has a proximal end 28 and a distal end 30, with a plurality of flow orifices 32 arranged along the distal end 30 to receive fluids from a relatively broad area of the internal wound site 12. The proximal end 22 of the infusion catheter 16 is generally nested within the proximal end 28 of the aspiration catheter 18 so that medication moves toward the internal wound site 12 through the infusion catheter 16, and fluids are removed from the internal wound site 12 through the distal end 30 of the aspiration catheter 18, and then through the generally annular space between the proximal ends 22, 28 of the catheters 16, 18.

Figure 2:
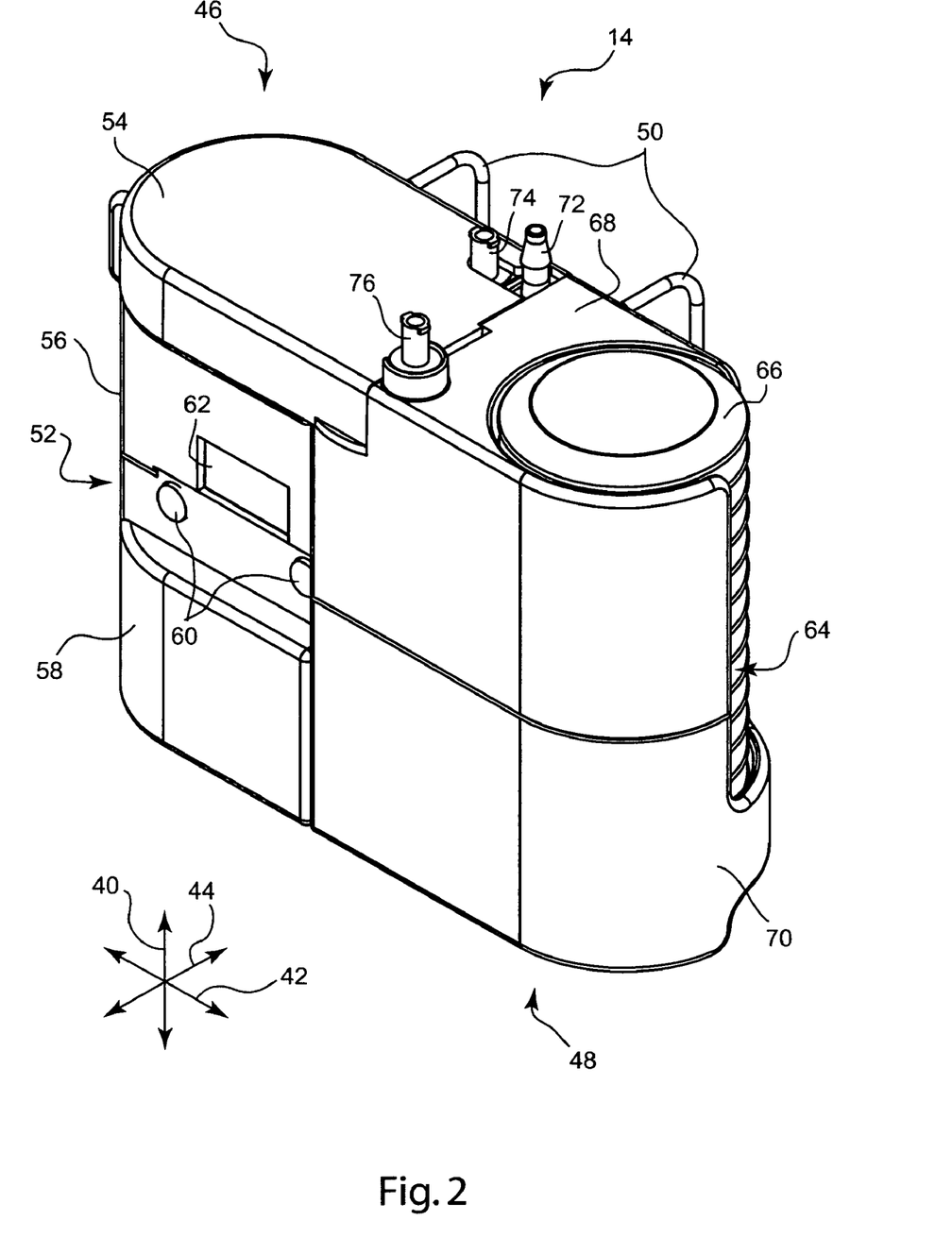
FIG. 2 is a perspective view of the integrated infusion and aspiration system of FIG. 1, in a fully-assembled state.

Referring to FIG. 2, a perspective view illustrates the infusion unit 14 of the system 10 of FIG. 1, without the catheters 16, 18. The infusion unit 14 has a longitudinal direction 40, a lateral direction 42, and a transverse direction 44, which are oriented as illustrated by the arrows in FIG. 2. The infusion unit 14 has a controller 46 and a reservoir module 48. The reservoir module 48 contains medication to be provided to the internal wound site 12 and fluids aspirated from the internal wound site 12. The controller 46 provides the necessary pressure differentials to control infusion of medication to the internal wound site 12 and aspiration of fluids from the internal wound site 12. The infusion unit 14 may also have a pair of mounting brackets 50 or other attachment devices that can be used to attach the infusion unit 14 to a mobile rack, hospital bed frame, or other piece of hospital equipment.

The controller 46 has a main body 52 that contains most of the internal components (not shown) of the controller 46, and a cap 54 that can be removed to couple the controller 46 to the reservoir module 48 in a manner that will be shown and described in greater detail subsequently. The main body 52 has a first portion 56 and a second portion 58 that are attached together via relative motion in the longitudinal direction 40 to encase the internal components. The controller 46 has controls such as buttons 60 that can be used by medical personnel to control the operation of the controller 46. Additionally, the controller 46 may have a display 62 that may show information such as infusion and aspiration history, the current operational mode of the controller 46, and the like.

The reservoir module 48 has a reservoir retainer 64 that serves to retain a first reservoir (not shown in FIG. 2) and a second reservoir 66. The first reservoir contains medication to be infused into the internal wound site 12 and the second reservoir 66 receives fluid aspirated from the internal wound site 12. The reservoir retainer 64 has a first portion 68 and a second portion 70 that are attached together along the longitudinal direction 40 in a manner similar to that of the first and second portions 56, 58 of the main body 52 of the controller 46. Additionally, the reservoir module 48 has an infusion port 72 shaped to be connected to the proximal end 22 of the infusion catheter 16 and an aspiration port 74 shaped to be connected to the proximal end 28 of the aspiration catheter 18. A fill port 76 is shaped to be connected to a supply of medication to enable the first reservoir to be filled without removing it from the reservoir retainer 64.

The controller 46 and the reservoir module 48 are coupled together in a manner that is simple and relatively failsafe, for example, through the use of mating surfaces (not shown) of the controller 46 and the reservoir module 48 that interlock via dovetail features or the like. The controller 46 may be coupled to any of multiple reservoir modules, not all of which need have the same configuration as the reservoir module 48. For example, in alternative embodiments of the invention, a reservoir module may have only a single reservoir for infusion. The controller 46 may be connectable to such a reservoir module in a manner similar to that of the reservoir module 48.

When the controller 46 and the reservoir module 48 are coupled together, the controller 46 limits flow of the medication from the reservoir module 48. The controller 46 may utilize peristaltic pumping so that medication us unable to flow into the infusion catheter 16 in the absence of pumping action by the controller 46. It is desirable to have a valve that prevents medication flow into the infusion catheter 16 in the event that the reservoir module 48 is not properly coupled to the peristaltic pumping components (not shown in FIG. 2) of the controller 46. Such a valve prevents the delivery of excess medication by ensuring that medication can flow only when the peristaltic pumping components are properly engaged to limit medication flow. One embodiment of such a valve will be shown and described in connection with FIGS. 3, 4, and 5, as follows.

Figure 3:
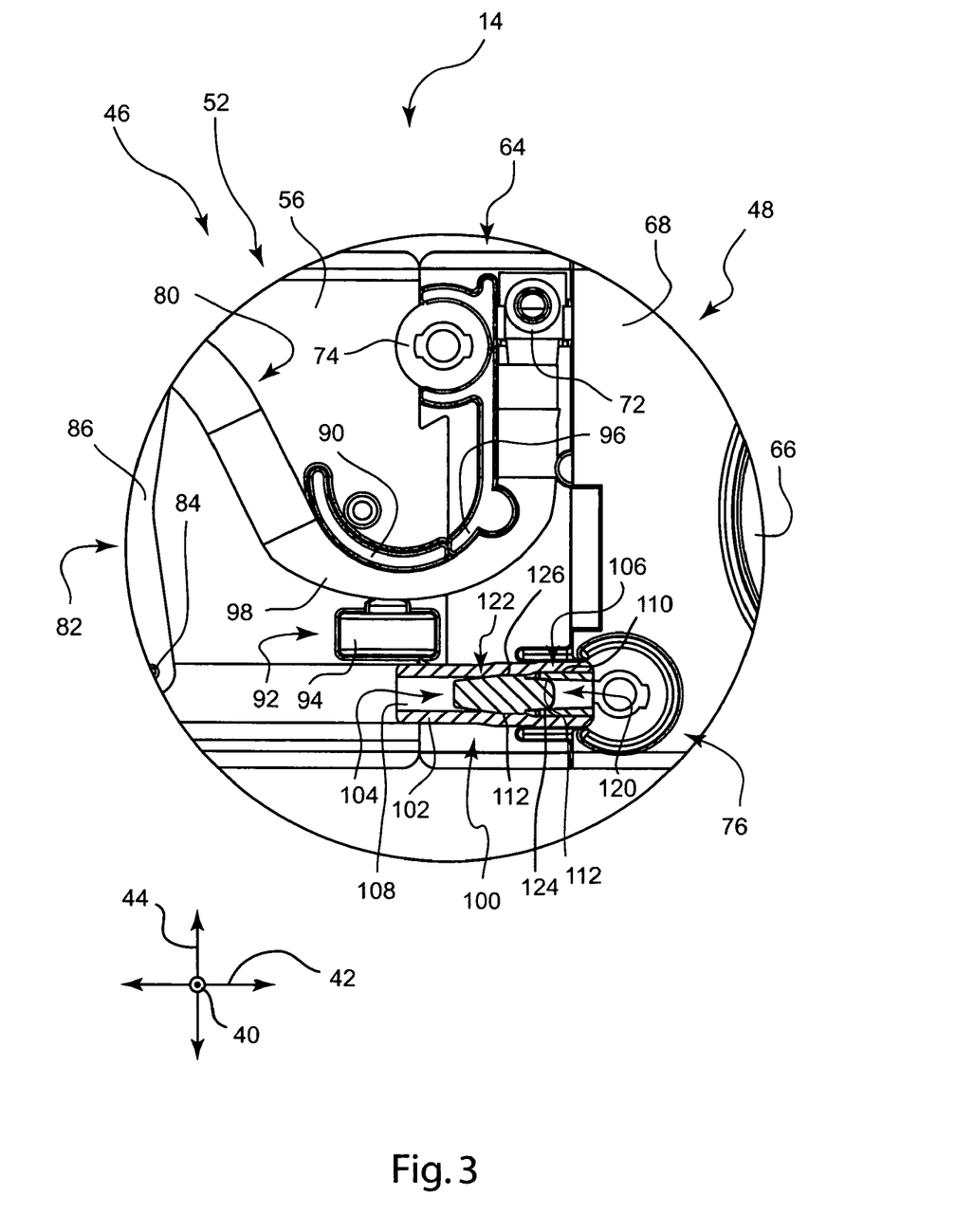
FIG. 3 is an enlarged, plan view of a portion of the infusion unit of the integrated infusion and aspiration system of FIG. 1, with a portion of the infusion unit sectioned to illustrate a tension-activated valve.

Referring to FIG. 3, a plan view illustrates the upper end of the infusion unit 14 with the cap 54 withdrawn to reveal internal components. As shown, the reservoir module 48 has a conduit, which may take the form of a tube 80, that extends in a generally circular pathway from a location in communication with the fill port 76 to convey medication to the infusion port 72. In this application, the term "conduit" refers to a fluid conveying structure with any cross sectional shape. Accordingly, a "conduit" need not necessarily be a tube.

The controller 46 has a pump 82, which may take the form of a peristaltic pump designed to compress a portion of the tube 80 and to move the compressed portion along the tube 80 to urge the medication to move through the tube 80 in a highly controllable manner. The pump 82 may include a plurality of rotor pins 84, only one of which is visible in FIG. 3. The rotor pins 84 are retained by a rotor carriage 86 that rotates about an axis of rotation 88 to move the rotor pins 84 along a circular path. The rotor carriage 86 may have a generally triangular shape and may carry three rotor pins 84. The rotor carriage 86 is driven by a motor (not shown in FIG. 3) that provides rotational output about an axis of rotation.

The rotor pins 84 may take the form of small-diameter cylindrical rollers that are able to roll along the exterior of the tube 80. The tube 80 may be "tightly routed," or stretched tightly around the rotor pins 84 such that the tube 80 is pinched relatively tightly proximate each of the rotor pins 84, so that, when the tube 80 is properly engaged by the pump 82, medication is generally unable to flow into the infusion catheter 16 in the absence of motion of the rotor pins 84. The cap 54 is generally shaped to cover the tube 80, the rotor pins 84, and the rotor carriage 86 to prevent external objects from interfering with the operation of the pump 82.

The present invention envisions the use of a wide variety of different types of pumps. For example, peristaltic pumps need not involve stretching of a conduit about the rotor pins, but may instead be based upon compression of the conduit by the rotor pins against an opposing surface, such as a generally cylindrical interior wall. Indeed, a controller according to the present invention need not have a peristaltic pump, but may instead use a different type of pump such as a screw pump, a rotary vane pump, a rod-and-piston pump, or any other known type of pump. Indeed, the present invention may be useful in any situation in which it is desirable to prevent fluid flow in the absence of tension, regardless of whether a pump is present within the system.

The controller 46 also has a constraining member in the form of an arcuate wall 90 that abuts a portion of the tube 80 to control the path of the tube 80 around the rotor pins 84. The arcuate wall 90 also causes the tube 80 to assume a generally oval cross section proximate the arcuate wall to enhance the operation of a blockage sensor 92. The blockage sensor 92 is designed to sense preferential distention of the portion of the tube 80 proximate the arcuate wall 90 to determine whether the tube 80 or the infusion catheter 16 has been pinched or blocked. Accordingly, the blockage sensor 92 includes a switch that either closes or opens a circuit in response to abnormal distention of the tube 80. Closing or opening the circuit may trigger cessation of infusion and/or aspiration, production of an audible alarm tone, or the like.

In FIG. 3, the switch of the blockage sensor 92 takes the form of a button 94 that can be compressed to cause conductors within the button 94 to either contact each other, thereby closing the circuit. The button 94 may extend upward from a circuit board (not shown) that controls the operation of the controller 46 and lies generally coplanar with the display 62 illustrated in FIG. 2. Indeed, the circuit board may have a continuous expanse of substrate that extends from behind the display 62 into the button 94.

The reservoir module 48 may have a second constraining member, which takes the form of an arcuate wall 96 adjoining the arcuate wall 90 of the controller 46. The arcuate walls 90, 96 may provide a relatively continuous surface about which the tube 80 bends at a relatively constant radius. The arcuate walls 90, 96 operate to broaden the adjoining portion of the tube 80 along the longitudinal direction 40, while constraining the adjoining portion along the lateral and transverse directions 42, 44 to provide a constrained portion 98 of the tube 80. The existence of the constrained portion 98 enhances operation of the blockage sensor 92 by magnifying the distention of the tube 80 measured by the blockage sensor 92.

As shown, the reservoir module 48 also has a tension-activated valve 100, or valve 100, that permits flow into the tube 80 only when the tube 80 is under tension. The valve 100 lies at the junction of the tube 80 with the fill port 76, and prevents medication from flowing from the fill port 76 into the tube 80 when the tube 80 is not under tension. Accordingly, the valve 100 is opened when the tube 80 is routed tightly about the rotor pins 84 as shown in FIG. 3, and is closed when the tube 80 is not engaged by the pump 82. When the tube 80 is engaged by the pump 82, the pump 82 limits flow of medication through the tube 80 medication is generally unable to flow past the rotor pins 84 in the absence of rotor motion. When the tube 80 is not engaged by the pump 82, the valve 100 prevents flow. Accordingly, medication is not allowed to flow freely into the infusion catheter 16, regardless of whether the tube 80 is engaged by the pump 82.

The valve 100 may have a number of components, one of which is a wall 102 of the tube 80 proximate the end of the tube 80 adjoining the fill port 76. Additionally, the valve 100 includes a plunger 104 and a valve seat 106. The plunger 104 generally engages the valve seat 106 to prevent flow, and is removed from the valve seat 106 to permit flow. The plunger 104 is retained within a bore 108 of the tube 80. In this application, a "plunger" and a "valve seat" are any two structures that can be brought into contact with each other to impede fluid flow. In certain embodiments, such as the valve 100, the plunger may be moveable while the valve seat is stationary. In alternative embodiments, a movable valve seat may be used in addition to or in the alternative to a movable plunger.

In the embodiment of FIG. 3, the valve seat 106 is integrally formed with the fill port 76. The valve seat 106 has a generally tubular configuration. Accordingly, the valve seat 106 has an outer surface 110 and an inner surface 112. The end portion of the wall 102 of the tube 80 relatively tightly engages the outer surface 110, and may also be bonded, ultrasonically welded, clamped, or otherwise attached to the outer surface 110 to ensure that the wall 102 is not disengaged from the outer surface 110 during assembly or operation of the infusion unit 14. Medication is able to flow from the fill port 76 into the adjacent end of the tube 80 through the inner surface 112. Additionally, the plunger 104 is able to seat against the inner surface 112 to prevent flow in the absence of tension in the tube 80.

As shown, the plunger 104 has a sealing end 120 and a retention end 122. The retention end 122 keeps the plunger 104 in place within the bore 108 of the tube 80, while the sealing end 120 seats against the inner surface 112 to keep medication from flowing past the plunger 104 when the valve 100 is closed. Use of the phrase "sealing end" does not require that the valve 100 provide a perfect, fluid-tight seal; a perfect seal may not be necessary to avoid the delivery of unsafe quantities of medication to the internal wound site 12. However, a perfect seal may be desirable to prevent any undesired medication flow to the internal wound site 12.

The sealing end 120 has a contact surface 124 that has a generally frusto-conical shape. The contact surface 124 is able to contact the inner surface 112 in such a manner that medication is substantially unable to move through the contacting portions of the contact surface 124 and the inner surface 112. The retention end 122 is sized slightly larger than the uncompressed diameter of the bore 108 so that the retention end 122 is relatively tightly gripped by the wall 102 of the tube 100. Accordingly, the plunger 104 does not move significantly along the axis of the tube 80, despite the existence of oscillating levels of tension on the tube 80 and pressure differentials across the plunger 104 during operation of the infusion unit 14. The retention end 122 has splines 126 that permit fluid to flow past the retention end 122 in a manner that will be shown and described in connection with FIGS. 4 and 5.

Figure 4:
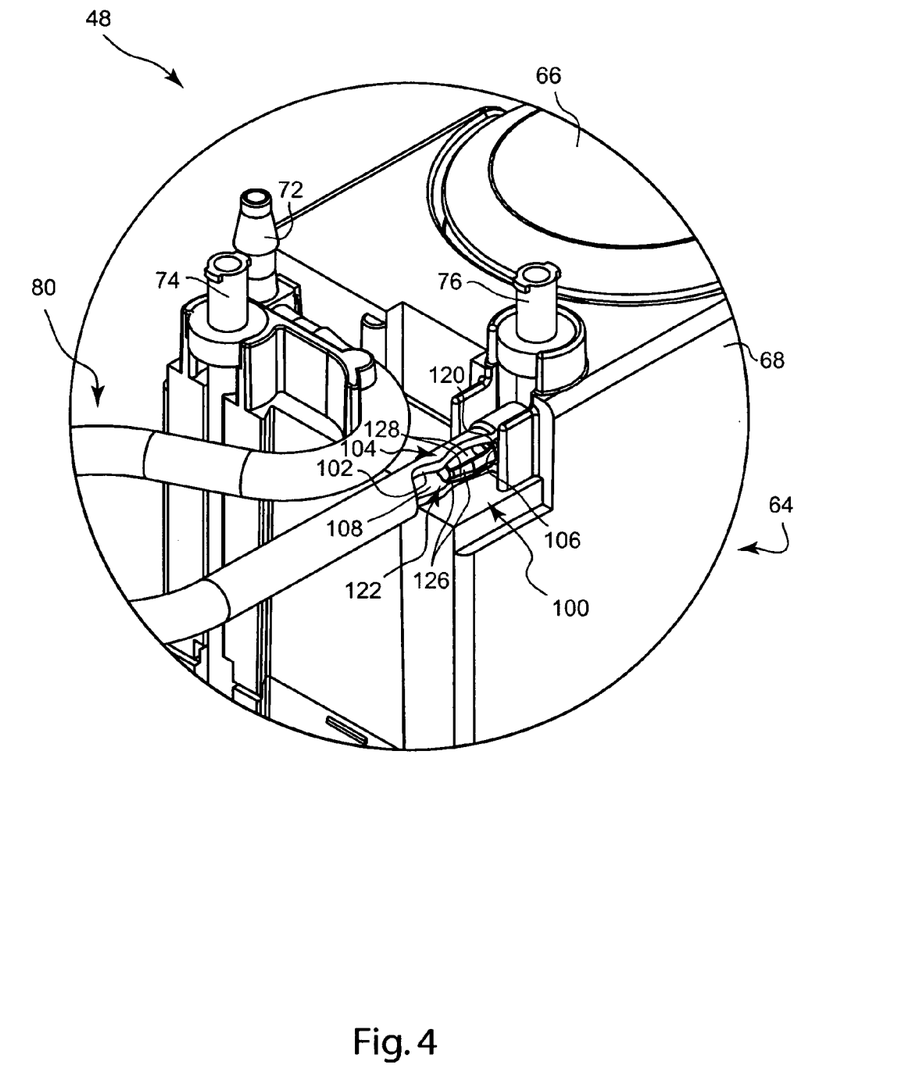
FIG. 4 is a perspective view of a portion of the reservoir module of the integrated infusion and aspiration system of FIG. 1, with a portion of the tube cut away to illustrate the valve in the closed position.

Referring to FIG. 4, an enlarged, perspective view illustrates the top portion of the reservoir module 48 of the infusion unit 14 of FIGS. 1, 2, and 3, with the valve 100 in the closed configuration. As shown, the infusion unit 14 has been removed from the controller 46. Thus, the tube 80 is not engaged by the pump 82 (not shown in FIG. 4). Accordingly, the tube 80 is not under significant tension, and the valve 100 is closed.

A portion of the tube 80 has been cut away to illustrate the plunger 104 and a small portion of the valve seat 106 of the valve 100. In FIG. 4, the sealing end 120 is relatively tightly seated in the valve seat 106. The portion of the wall 102 of the tube 80 between the splines 126 and the attachment of the tube 80 to the valve seat 106 is resilient (like the remainder of the tube 80), and is slightly stretched so as to urge the sealing portion 120 of the plunger 104 into engagement with the valve seat 106. There is no additional tension on the tube 80 to counteract this resilient force, so the valve 100 remains in the closed configuration.

As shown in FIG. 4, the splined shape of the retention end 122 of the plunger 104 defines a plurality of passageways 128 that extend along the lateral direction 42, between the splines 126. The passageways 128 permit medication to flow past the retention end 122 when the valve 100 is in the open position. In this application, a "splined shape" is a shape with a plurality of grooves and/or ridges distributed relatively about its perimeter.

In order to deliver medication from the reservoir module 48 to the internal wound site 12, the reservoir module 48 needs to be coupled to the controller 46. Attachment of the reservoir module 48 to the controller 46 is relatively simple, and may be performed by sliding mating dovetail features of the controller 46 and the reservoir module 48 into engagement with each other along the longitudinal direction 40. The tube 80 is then positioned in engagement with the pump 82 to open the valve, as will be shown and described in greater detail in connection with the discussion of FIG. 5.

Figure 5:
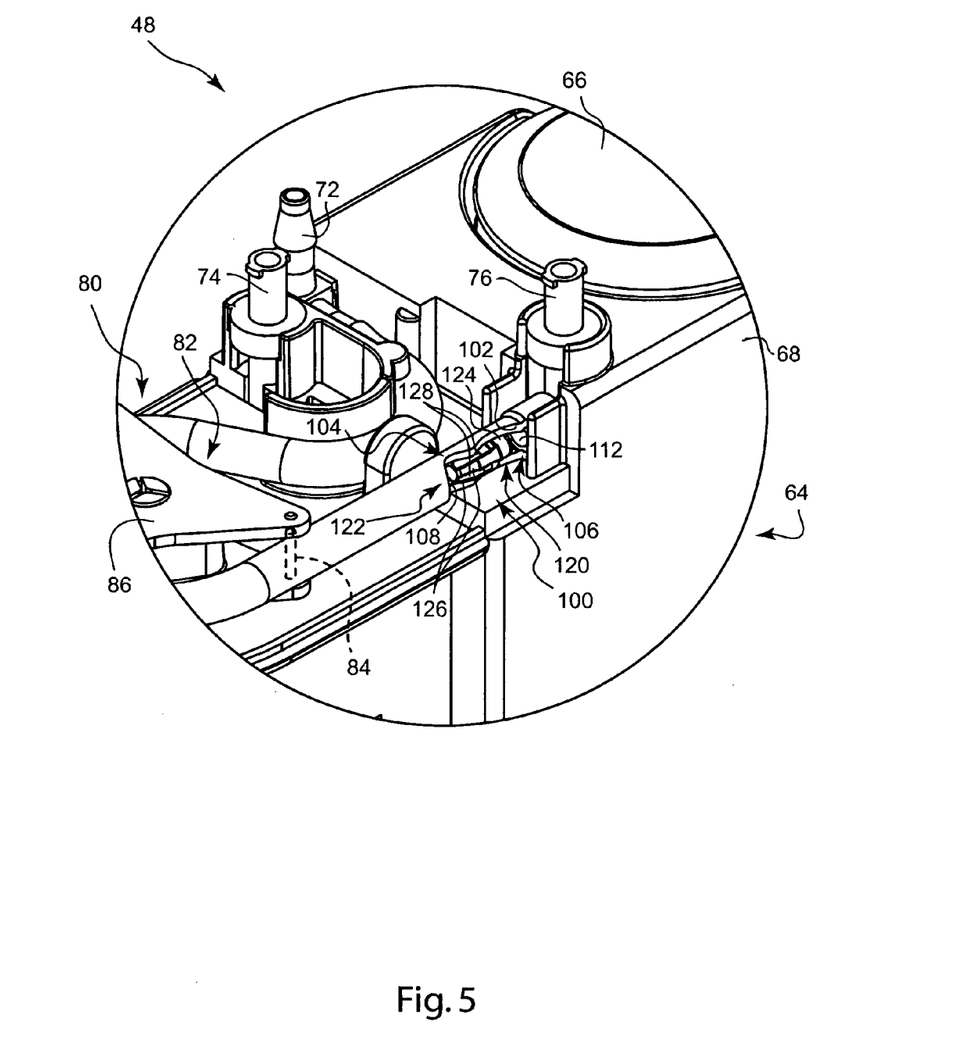
FIG. 5 is a perspective view of a portion of the integrated infusion and aspiration system of FIG. 1, with a portion of the tube cut away to illustrate the valve in the open position.

Referring to FIG. 5, an enlarged, perspective view illustrates the top portion of the reservoir module 48 of the infusion unit 14 of FIGS. 1, 2, and 3, with the valve 100 in the open configuration to permit medication to flow toward the internal wound site 12. As the tube 80 is stretched relatively tightly about the rotor pins 84, the rotor pins 84 pinch the tube 80 to impede fluid flow through the tube 80. Medication is generally able to flow through the tube 80 only to the extent that the rotor carriage 86 rotates to move the rotor pins 84 along the curvature of the tube 80. This tension on the tube 80 remains while the tube 80 is engaged by the pump 82, regardless of whether the pump 82 is operating.

When the tube 80 is stretched around the rotor pins 84, the resulting tension in the tube 80 opens the valve 100. More precisely, the portion of the tube 80 between the retention end 122 of the plunger 104 and the valve seat 106 stretches in response to the tension in the tube 80 caused by engagement of the pump 82 and the tube 80. The elongation of the portion of the tube 80 between the retention end 122 of the plunger 104 and the valve seat 106 enables the contact surface 124 of the sealing end 120 of the plunger 104 to be withdrawn from contact with the inner surface 112 of the valve seat 106. Withdrawal of the contact surface 124 from the inner surface 112 opens the valve 100 by providing an annular gap between the contact surface 124 and the inner surface 112. Medication is then able to enter the tube 80 by flowing through the annular gap, and then flowing through the passageways 128 to pass through the retention end 122.

Thereafter, the relatively constant tension on the tube 80 causes the valve 100 to remain open until the tube 80 is disengaged from the pump 82. Accordingly, medication flow through the tube 80 is always either controlled by the pump 82, or substantially blocked via closure of the valve 100, and the infusion unit 14 is unable to provide an unregulated flow of medication into the infusion catheter 16.

In the alternative to the configuration illustrated in FIG. 5, the valve 100 may be positioned at the junction of the tube 80 with the infusion port 72. In such a position, the valve 100 would not impede fluid flow into the tube 80, but would instead block fluid flow from the tube 80 to the infusion port 72 when the tube 80 is not under tension. The valve 100 itself may be configured substantially as shown in FIG. 5 and the preceding figures, and would open in response to tension in substantially the same manner set forth above.

Notably, fluid flow into the tube 80 is substantially independent of any pressure gradient that exists within the fluid. Such a pressure differential would have to be large enough to overcome the resilient force of the portion of the tube 80 between the retention end 122 of the plunger 104 and the valve seat 106. The resilient force exerted by this portion of the tube 80 is generally large enough to keep the plunger 104 seated in the valve seat 106 until the tube 80 is tensioned 80, despite pressure rises that may be expected to occur within the fluid supply. Thus, the valve 100 does not operate as a check valve, and is not generally subject to accidental opening in response to a pressure rise in the fluid within the fill port 76, as may occur when the unit 14 is dropped or knocked, for example.

The systems and methods of the present invention may be applied to a wide variety of applications in which it may be desirable to control fluid flow based on the tension in a member. Fluid flow may more precisely be controlled based on the tension in a conduit that conveys the fluid. Such a valve system is not limited to use in medication infusion systems, but is broadly applicable in a variety of fields such as hydraulics, consumer products, and manufacturing systems.

Furthermore, a wide variety of configurations may be used in place of the valve 100 of FIGS. 3-5 to provide tension-based fluid control. In some applications, it may be desirable to provide a valve that is closed, not opened, in response to tension in a conduit. For example, those of skill in the art will recognize that the plunger 104 and/or the valve seat 106 may be repositioned and/or reconfigured to provide a valve (not shown) that is open in the absence of tension in the tube 80, and closed when tension is applied to the tube 80. Furthermore, in certain configurations, a stretchable conduit need not be present to cause the valve to operate. Some exemplary alternative embodiments will be shown and described in connection with FIGS. 6-10, as follows.

Figure 6:
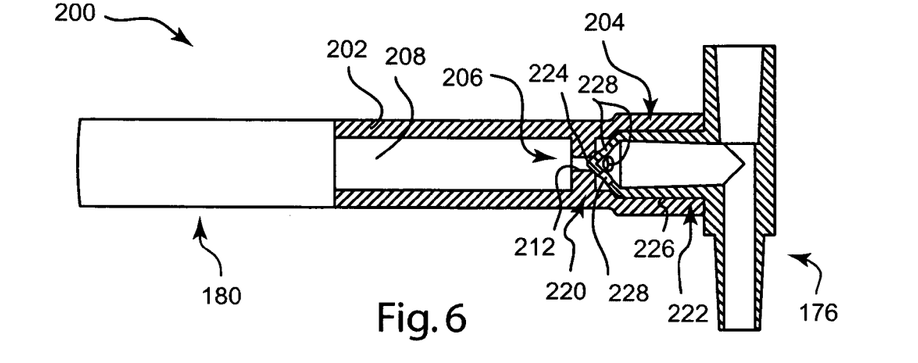
FIG. 6 is a partially-sectioned view of a valve of an infusion system according to one alternative embodiment of the invention.

Referring to FIG. 6, a fill port 176 and a tube 180 may be parts of an infusion system like the infusion system 10 of FIG. 1, and may thus be incorporated into an infusion unit such as the infusion unit 14. The tube 180 may be designed for engagement by a peristaltic pump like the pump 82. Accordingly, a valve 200 may be provided to control fluid flow from the fill port 176 to the tube 180 to serve a function similar to that of the valve 100. For clarity, the fill port 176, tube 180, and valve 200 are illustrated in isolation in the side elevation, section view of FIG. 6.

As shown, the tube 180 has a wall 202, a portion of which is incorporated into the valve 200. The valve 200 also includes a plunger 204 and a valve seat 206. The plunger 204 is integrally formed with the fill port 176, and the valve seat 206 is integrally formed with the wall 202, so that the valve seat 206 defines a stepped-down portion of a bore 208 of the tube 180. Accordingly, the valve seat 206 has an inner surface 212 defining a bore smaller than the remainder of the bore 208 of the tube 180.

The plunger 204 has a sealing end 220 designed to seat against the valve seat 206, and a retention end 222 designed to retain the tube 180. More precisely, the sealing end 220 has a contact surface 224 with a generally conical shape. The contact surface 224 is positioned within the bore 208 of the tube 180, and is slidable into engagement with the inner surface 212 of the valve seat 206 to block fluid flow through the valve seat 206. The retention end 222 has an outer surface 226 that is generally cylindrical in shape. The outer surface 226 is sized slightly larger than the nominal diameter of the bore 208 so that the tube 180 must stretch radially to fit around the outer surface 226. Thus, the tube 180 grips the outer surface 226. If desired, an adhesive, ultrasonic weld, clamp, or the like (not shown) may be applied to strengthen the attachment of the tube 180 to the outer surface 226.

In addition to the contact surface 224, the sealing end 220 has a plurality of passageways 228, which may take the form of holes passing through the contact surface 224. The passageways 228 pass through the portion of the contact surface 224 that lies outside the valve seat 206 when the contact surface 224 is pressed against the valve seat 206 so that, when the contact surface 224 is seated against the valve seat 206, fluid is unable to pass from the passageways 228 through the valve seat 206. Only three passageways 228 are illustrated in the section view of FIG. 6 to provide a total of four passageways 228, but any number of passageways may be used.

In the configuration of FIG. 6, the valve 200 is in the closed configuration. Accordingly, the contact surface 224 abuts the adjacent rim of the inner surface 212 of the valve seat 206 along a generally annular sealing interface to prevent fluid from entering the tube 180 from within the fill port 176. When the tube 180 is stretched around the rotor pins 84, the resulting tension in the tube 180 opens the valve 200.

More precisely, the portion of the tube 180 between the valve seat 206 and the outer surface of the plunger 204 stretches in response to the tension in the tube 180 caused by engagement of the pump 82 and the tube 180. The resulting elongation of the tube 180 withdraws the valve seat 206 from contact with the contact surface 224 of the sealing end 220 of the plunger 204. Withdrawal of the valve seat 206 from the contact surface 224 opens the valve 200 by providing an annular gap between the contact surface 224 and the inner surface 212. Medication is then able to enter the tube 180 from the fill port 176 by flowing through the passageways 228, then flowing through the annular gap to pass through the valve seat 206.

Figure 7:
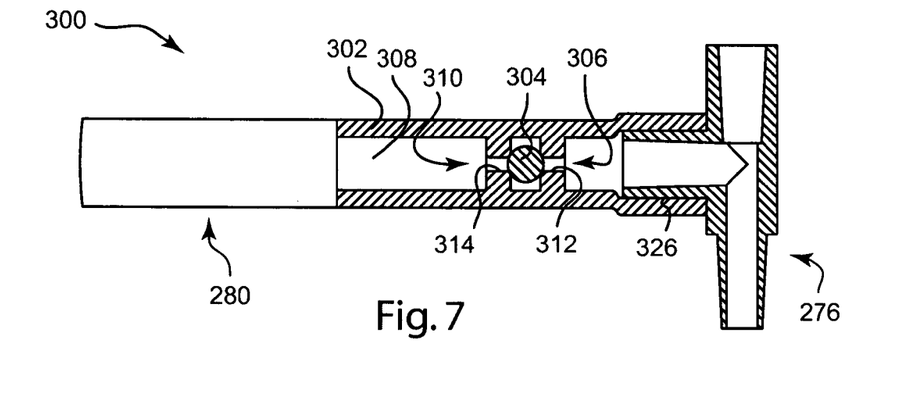
FIG. 7 is a partially-sectioned view of a valve of an infusion system according to another alternative embodiment of the invention.

Referring to FIG. 7, a fill port 276 and a tube 280 may be parts of an infusion system like the infusion system 10 of FIG. 1, and may thus be incorporated into an infusion unit such as the infusion unit 14. The tube 280 may be designed for engagement by a peristaltic pump like the pump 82. Accordingly, a valve 300 may be provided to control fluid flow from the fill port 276 to the tube 280 to serve a function similar to that of the valve 100. For clarity, the fill port 276, tube 280, and valve 300 are illustrated in isolation in the side elevation, section view of FIG. 7.

As shown, the tube 280 has a wall 302, a portion of which is incorporated into the valve 300. The valve 300 also includes a plunger 304 and a first valve seat 306. The plunger 304 is generally spherical and is sized to fit within a bore 308 of the tube 280 with clearance so that the plunger 304 is movable within the bore 308. The valve 300 also includes a second valve seat 310 positioned such that the plunger 304 rests between the first and second valve seats 306, 310. Each of the valve seats 306, 310 is integrally formed with the bore 308 of the tube 280. Additionally, each of the first and second valve seats 306, 310 has an inner surface 312, 314, respectively. The valve seats 306, 310 provide stepped down portions of the bore 280 so that each of the inner surfaces 312, 314 defines a bore smaller than the remainder of the bore 308 of the tube 280.

The fill port 276 has an outer surface 326 that is generally cylindrical in shape. The outer surface 326 is sized slightly larger than the nominal diameter of the bore 308 so that the tube 280 must stretch radially to fit around the outer surface 326. Thus, the tube 280 grips the outer surface 326. If desired, an adhesive, ultrasonic weld, clamp, or the like (not shown) may be applied to strengthen the attachment of the tube 280 to the outer surface 326.

In the configuration of FIG. 7, the valve 300 is in the closed configuration. Accordingly, the plunger 304 abuts the adjacent rims of the inner surfaces 312, 314 of the first and second valve seats 306, 310 along generally annular sealing interfaces to prevent fluid from passing through the valve seats 312, 314 to enter the tube 280 from within the fill port 276. The length of the tube 280 between the valve seats 312, 314 is short enough that the valve seats 312, 314 press against opposite sides of the plunger 304 to keep the plunger 304 centered within the bore 308 and provide the seals. The plunger 304 abuts both of the valve seats 306, 310 to redundantly restrict fluid flow into the tube 280. When the tube 280 is stretched around the rotor pins 84, the resulting tension in the tube 280 opens the valve 300.

More precisely, the portion of the tube 280 between the first and second valve seats 306, 310 stretches in response to the tension in the tube 280 caused by engagement of the pump 82 and the tube 280. The resulting elongation of the tube 280 draws the valve seats 306, 310 apart to provide gaps between the valve seats 306, 310 and the plunger 304. Medication is then able to enter the tube 280 from the fill port 276 by flowing through the first valve seat 306, flowing around the plunger 304, and then flowing through the second valve seat 310. The motion of the fluid through the valve 300 may tend to keep the plunger 304 generally centered within the space between the valve seats 306, 310 to maintain the gaps between the valve seats 306, 310 and the plunger 304, thereby enabling the fluid to continue to flow efficiently through the valve 300.

Figure 8:
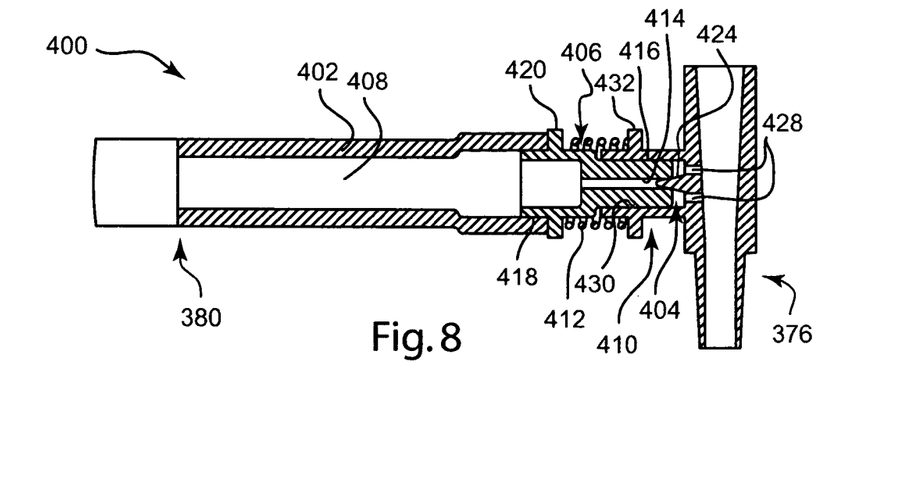
FIG. 8 is a partially-sectioned view of a valve of an infusion system according to another alternative embodiment of the invention.

Referring to FIG. 8, a fill port 376 and a tube 380 may be parts of an infusion system like the infusion system 10 of FIG. 1, and may thus be incorporated into an infusion unit such as the infusion unit 14. The tube 380 may be designed for engagement by a peristaltic pump like the pump 82. Accordingly, a valve 400 may be provided to control fluid flow from the fill port 376 to the tube 380 to serve a function similar to that of the valve 100. For clarity, the fill port 376, tube 380, and valve 400 are illustrated in isolation in the side elevation, section view of FIG. 8.

As shown, the tube 380 has a wall 402, a portion of which is incorporated into the valve 400. The valve 400 also includes a plunger 404 and a valve seat 406. The plunger 404 is a generally conical structure integrally formed with the fill port 376 and oriented toward the tube 380. The valve seat 406 is generally tubular in shape, and may be formed of a rigid plastic, metal, or the like. One end of the valve seat 406 is seated in a bore 408 of the tube 380, as shown, so that the valve seat 406 essentially forms a rigid extension of the tube 380. The valve 400 also has a rigid tubular body 410 that is integrally formed with the fill port 376, and has a generally tubular shape concentric with the valve seat 406. One end of the valve seat 406 is slidable into the interior of the rigid tubular body 410, and is biased toward the plunger 404 by a resilient member, which may take the form of a tension spring 412.

The valve seat 406 has an inner surface 414 that defines a relatively constricted bore in communication with the bore 408 of the tube 380. Further, the valve seat 406 has a first outer surface 416, a second outer surface 418, and a retention flange 420. The outer surfaces 416, 418 are both generally cylindrical in shape, and the first outer surface 416 is sized to slide into the bore of the rigid tubular body 410. The second outer surface 418 is sized slightly larger than the nominal diameter of the bore 408 so that the tube 380 must stretch radially to fit around the second outer surface 418. Thus, the tube 380 grips the second outer surface 418. If desired, an adhesive, ultrasonic weld, clamp, or the like (not shown) may be applied to strengthen the attachment of the tube 380 to the second outer surface 418.

The retention flange 420 serves to anchor one end of the tension spring 412 against the valve seat 406. The adjacent end of the tension spring 412 may be adhesive bonded, insert molded, or otherwise attached to the retention flange 420. In the alternative, a portion of the adjacent end of the tension spring 412 may extend behind the retention flange 420.

The plunger 404 has a contact surface 424, which may be generally conical in shape. The contact surface 424 is shaped to contact the inner surface 414 of the valve seat 406 to prevent fluid from flowing into the valve seat 406 when the contact surface 424 abuts the inner surface 414. The plunger 404 is centered between a plurality of passageways 428 that enable fluid to enter the rigid tubular body 410 by flowing around the plunger 404. If the contact surface 424 of the plunger 404 is not positioned to abut the inner surface 414 of the valve seat 406, the fluid is able to flow from the rigid tubular body 410 into the valve seat 406, and from the valve seat 406 into the tube 380.

As shown, the rigid tubular body 410 has an inner surface 430 and a retention flange 432. The inner surface 430 is generally cylindrical and is sized to receive the first outer surface 416 of the valve seat 406 with clearance so that the valve seat 406 is able to slide into and out of the rigid tubular body 410. However, the inner surface 430 may be sized closely enough to the first outer surface 416 so that a seal is provided between the inner surface 430 and the first outer surface 416 to keep fluid from leaking from the valve 400 by flowing between the first outer surface 416 and the inner surface 430.

The retention flange 432 anchors the end of the tension spring 412 opposite to that anchored by the retention flange 420 of the valve seat 406. The adjacent end of the tension spring 412 may be adhesive bonded, insert molded, or otherwise attached to the retention flange 420. Alternatively, the adjacent end of the tension spring 412 may simply extend behind the retention flange 432. In any case, the retention flanges 420, 432 cooperate to retain the tension spring 412 in such a manner that the tension spring 412 tends to draw the valve seat 406 into the rigid tubular body 410. Thus, the tension spring 412 presses the valve seat 406 against the plunger 404 to block fluid flow into the valve seat 406.

In the configuration of FIG. 8, the valve 400 is in the closed configuration. Accordingly, the plunger 404 abuts the adjacent rim of the inner surface 414 of the valve seats 406 along a generally annular sealing interface to prevent fluid from passing through the valve seat 406 to enter the tube 380 from within the fill port 376. When the tube 380 is stretched around the rotor pins 84, the resulting tension in the tube 380 opens the valve 400.

More precisely, tension on the tube 380 tends to pull the valve seat 406 away from the rigid tubular body 410. Relative motion between the valve seat 406 and the rigid tubular body 410 is generally proportional to the tension in the tube 380, and is limited by the counteracting tension provided by the tension spring 412. As a result of relative motion between the valve seat 406 and the rigid tubular body 410, the valve seat 406 is drawn away from the plunger 404, and the inner surface 414 of the valve seat 406 is withdrawn from contact with the contact surface 424 of the plunger 404. A gap is provided between the valve seat 406 and the plunger 404, and medication is thus able to enter the tube 380 from the fill port 376 by flowing through the passageways 428, into the rigid tubular body 410, around the plunger 404, and through the valve seat 406.

The valve 400 of FIG. 8 is different from the embodiments described previously because it does not depend on elongation of the tube 380 to open the valve 400. Rather, the tube 380 can be substantially non-stretchable without impairing the operation of the valve 400 because relative motion between the plunger 404 and the valve seat 406 is derived from elongation of the tension spring 412. Thus, the valve 400 provides greater flexibility in the type of tube 380 that can be used.

Figure 9:
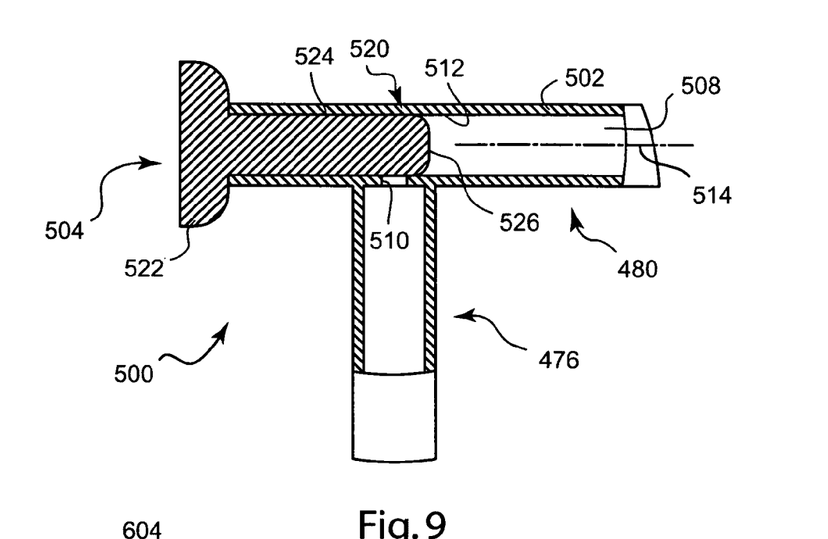
FIG. 9 is a partially-sectioned view of a valve of an infusion system according to yet another alternative embodiment of the invention.

Referring to FIG. 9, a supply tube 476 and a tube 480 may be parts of an infusion system like the infusion system 10 of FIG. 1, and may thus be incorporated into an infusion unit such as the infusion unit 14. The supply tube 476 may be provided in place of a fill port such as the fill port 76, or may be attached to such a fill port to operate in conjunction with it. The tube 480 may be designed for engagement by a peristaltic pump like the pump 82. Accordingly, a valve 500 may be provided to control fluid flow from the supply tube 476 to the tube 480 to serve a function similar to that of the valve 100.

For clarity, the supply tube 476, tube 480, and valve 500 are illustrated in isolation in the side elevation, section view of FIG. 9.

As shown, the tube 480 has a wall 502, a portion of which is incorporated into the valve 500. In the embodiment of FIG. 9, the valve 500 is designed to operate independently of engagement of a rigid valve seat with a rigid plunger. Rather, axial motion of a portion of the tube 480 is used to permit the valve 500 to open. This concept will be set forth in greater detail below.

The valve 500 has a blocking member 504 formed of a generally rigid material such as a plastic, and located partially within a bore 508 of the tube 480. An opening 510 is formed in the tube 480, in communication with a bore of the supply tube 476. As shown, the tube 480 has an inner surface 512 with a generally cylindrical shape with a diameter only slightly larger than the blocking member 504. The blocking member 504 and the inner surface 512 are generally coaxial, with axes of symmetry (not shown) aligned with an axis 514 of the tube 480.

In the embodiment of FIG. 9, the blocking member 504 has a sealing end 520 that controls fluid flow into the tube 480 and an anchoring end 522 at which the blocking member 504 is attached to some other stationary structure. The sealing end 520 has an outer surface 524 and a terminal surface 526. The outer surface 524 has a generally cylindrical shape that fits tightly enough within the inner surface 512 of the tube 480 that fluid is generally unable to flow between the inner surface 512 and the outer surface 524. However, there is sufficient clearance and/or surface smoothness between the outer surface 524 and the inner surface 512 to permit the tube 480 to slide along the axis 514 with respect to the blocking member 504. The inner surface 512 may be adhesive bonded, ultrasonically welded, clamped, or otherwise attached to the outer surface 524 proximate the anchoring end 522.

In the configuration of FIG. 9, the valve 500 is in the closed configuration. Accordingly, the opening 510 faces the outer surface 524 of the blocking member 504 such that the blocking member 504 blocks fluid flow into the tube 480 from the supply tube 476. When the tube 480 is stretched around the rotor pins 84, the resulting tension in the tube 480 opens the valve 500.

More precisely, the portion of the tube 480 between the anchoring end 522 and the opening 510 stretches in response to the tension in the tube 480 caused by engagement of the pump 82 and the tube 480. The resulting elongation of the tube 480 draws the opening 510 along the axis 514 until some or all of the opening 510 has moved beyond the terminal surface 526 of the sealing end 520 of the blocking member 504. The blocking member 504 is then no longer positioned to fully impede fluid flow through the opening 510. Consequently, medication is able to enter the tube 480 from the supply tube 476 by flowing through the opening 510, past the terminal surface 526.

As set forth above, the operation of the valve 500 is not dependent on engagement of a rigid plunger with a rigid valve seat. Rather, the valve 500 operates based on motion of the opening 510 along the axis 514 of the tube 480. Such motion occurs as a direct response to elongation of the tube 480.

Figure 10:
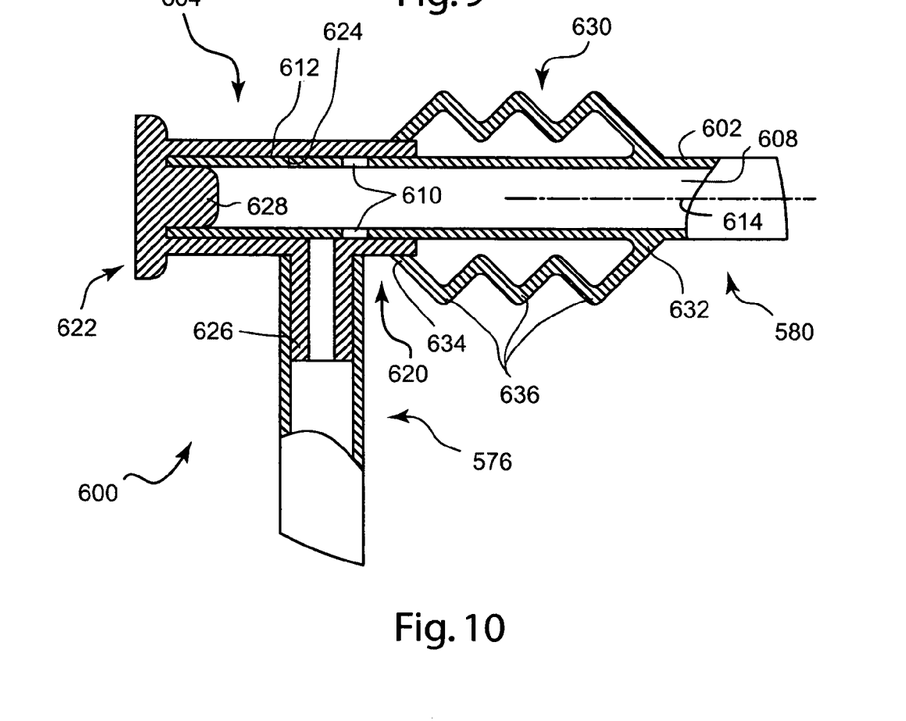
FIG. 10 is a partially-sectioned view of a valve of an infusion system according to still another alternative embodiment of the invention.

Referring to FIG. 10, a supply tube 576 and a tube 580 may be parts of an infusion system like the infusion system 10 of FIG. 1, and may thus be incorporated into an infusion unit such as the infusion unit 14. The supply tube 576 may be provided in place of a fill port such as the fill port 76, or may be attached to such a fill port to operate in conjunction with it. The tube 580 may be designed for engagement by a peristaltic pump like the pump 82. Accordingly, a valve 600 may be provided to control fluid flow from the supply tube 576 to the tube 580 to serve a function similar to that of the valve 100. For clarity, the supply tube 576, tube 580, and valve 600 are illustrated in isolation in the side elevation, section view of FIG. 10.

As shown, the tube 580 has a wall 602, a portion of which is incorporated into the valve 600. In the embodiment of FIG. 10, the valve 600 is designed to operate independently of engagement of a rigid valve seat with a rigid plunger. Rather, diametral contraction of a wall of the tube 580 in response to elongation is used to permit the valve 600 to open. This concept will be set forth in greater detail below.

The valve 600 has a blocking member 604 formed of a generally rigid material such as a plastic, and positioned to encase a portion of the tube 580. Two or more openings 610 are formed in the tube 580, in communication with the bore 608 of the tube 580. As shown, the tube 580 has an outer surface 612 with a generally cylindrical shape with a diameter only slightly smaller than the interior diameter of the blocking member 604. The blocking member 604 and the inner surface 612 are generally coaxial, with axes of symmetry (not shown) aligned with an axis 614 of the tube 580.

In the embodiment of FIG. 10, the blocking member 604 has a sealing end 620 that controls fluid flow into the tube 580 and an anchoring end 622 at which the blocking member 604 is attached to some other stationary structure. The sealing end 620 has an inner surface 624 and a supply tube receiver 626. The inner surface 624 has a generally cylindrical shape that fits tightly enough around the outer surface 612 of the tube 580 that fluid is generally unable to flow between the outer surface 612 and the inner surface 624 when the tube 580 is untensioned. However, when the tube 580 is under tension, diametral contraction of the tube 580 may cause there to be sufficient clearance between the inner surface 624 and the outer surface 612 to permit fluid flow between the inner surface 624 and the outer surface 612.

The outer surface 612 may be adhesive bonded, ultrasonically welded, clamped, or otherwise attached to the inner surface 624 proximate the anchoring end 622. The anchoring end 622 has a nub 628 that is shaped to fit into the bore 608 of the tube 580. The nub 628 may fit tightly enough into the bore 608 to prevent fluid flow between the nub 628 and the bore 608, thereby forming a seal that prevents fluid from escaping from the valve 600 via the anchoring end 622. The interior of the tube 580 may also be attached to the nub 628 via an adhesive, clamp, ultrasonic weld, or the like (not shown).

In the configuration of FIG. 10, the valve 600 is in the closed configuration. Accordingly, the outer surface 612 is pressed against the inner surface 624 proximate the openings 610 so that fluid is unable to enter the openings 610 from the supply tube 576. When the tube 580 is stretched around the rotor pins 84, the resulting tension in the tube 580 opens the valve 600.

More precisely, the tube 580 stretches in response to the tension in the tube 580 caused by engagement of the pump 82 and the tube 580. The resulting elongation of the tube 580 causes diametral contraction of the tube 580, i.e., motion of the wall 602 nearer the axis 614 of the tube 580. The openings 610 are also drawn toward the axis 614, and are therefore drawn away from the inner surface 624 of the sealing end 620 of the blocking member 604. Since the inner surface 624 no longer blocks fluid flow from the supply tube 576 into the openings 610, medication is able to enter the tube 80 from the supply tube 576 by flowing from the supply tube 576 along the space between the outer surface 612 and the inner surface 624, and then through the openings 610.

The tube 580 may have a sealing member 630 with a first end 632 that extends outward from the outer surface 612 and a second end 634 attached to the sealing end 620 of the blocking member 604. The sealing member 630 retains fluids that flow past the openings 610 and escape from between the outer surface 612 and the inner surface 624 when the valve 600 is open. The sealing member 630 has a plurality of ridges 636 that are relatively easily bendable to permit the first and second ends 632, 634 to move further from each other when the tube 580 stretches, and to move closer to each other again when tension is removed from the tube 580. The sealing member 630 effectively moves like a bellows to provide its sealing function regardless of the relative positions of the first and second ends 632, 634.

As set forth above, the operation of the valve 600 is not dependent on engagement of a rigid plunger with a rigid valve seat. Rather, the valve 600 operates based on motion of the openings 610 toward the axis 614 of the tube 580 as a result of diametral contraction of the tube 580. Such diametral contraction occurs as a direct response to elongation of the tube 580.

The present invention may be embodied in other specific forms without departing from its spirit or essential characteristics. Thus the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for percutaneous infusion of an internal wound site, the system comprising:
    a conduit positioned to convey a first fluid toward the internal wound site;
    a rotor positioned to impinge against the conduit to urge the first fluid to move through the conduit; and
    a valve positioned to impede flow of the first fluid through the conduit in response to absence of impingement of the rotor against the conduit, the valve comprising a rigid valve seat formed separately from the conduit and a rigid plunger movable along an axis of the conduit relative to the valve seat, wherein the valve extends coaxially with the conduit when the valve is in an open configuration, wherein the open configuration occurs in response to elongation of the conduit between the plunger and the valve seat.

2. The system of claim 1, further comprising a first reservoir shaped to contain the first fluid, wherein the conduit is coupled to the first reservoir to receive the first fluid from the first reservoir.

3. The system of claim 2, further comprising a second reservoir in communication with the internal wound site to receive a second fluid aspirated from the internal wound site.

4. The system of claim 1, wherein the rotor is incorporated into a peristaltic pump comprising multiple rotor pins, wherein the conduit is routed tightly about the rotor pins such that tension in the conduit causes opposing sides of the tube to press against each other proximate each of the rotor pins to impede flow of the first fluid past the rotor pins.

5. The system of claim 4, wherein the peristaltic pump is driven by a motor having an axis of rotation about which the rotor pins rotate.

6. The system of claim 1, wherein the valve operates substantially independently of a pressure gradient across the valve.

7. The system of claim 1, wherein the valve comprises a valve seat and a plunger, wherein the plunger is movable with respect to the valve seat such that the plunger contacts the valve seat to impede flow of the first fluid through the conduit.

8. The system of claim 7, wherein the conduit comprises a tube within which the valve seat and the plunger are retained, wherein elongation of a portion of the tube between the plunger and the valve seat enables the plunger to move with respect to the valve seat.

9. The system of claim 8, wherein the valve seat has a generally annular shape, wherein the plunger has a sealing end and a retention end, the sealing end having a tapered shape insertable into the valve seat to substantially prevent flow of the first fluid through the valve seat, the retention end having a splined shape selected to permit passage of the first fluid between the retention end and a bore of the tube.

10. The system of claim 8, wherein the valve seat has a generally annular shape, wherein the plunger has a sealing end and a retention end, the sealing end having a tapered shape insertable into the valve seat to substantially prevent flow of the first fluid through the valve seat, the retention end having a plurality of passageways formed therein to permit passage of the first fluid through the retention end.

11. The system of claim 8, wherein the valve seat comprises a first valve seat having a generally annular shape, wherein the plunger comprises a generally spherical shape, wherein the plunger is positioned to be pressed into engagement with the first valve seat via motion of a second valve seat having a generally annular shape.

12. The system of claim 7, wherein the valve further comprises a rigid tubular body, wherein one of the plunger and valve seat is attached to the rigid tubular body and the other of the plunger and valve seat is attached to the conduit, wherein the rigid tubular body is resiliently coupled to the conduit to enable the plunger to move with respect to the valve seat.

13. The system of claim 1, wherein the conduit has an opening oriented generally radially with respect to an axis of the conduit, wherein the valve comprises a blocking member positioned to block flow of the first fluid through the opening, wherein the opening moves along an axis of the tube with respect to the blocking member in response to elongation of the conduit to permit flow of the first fluid through the opening.

14. The system of claim 1, wherein the conduit has an opening oriented generally radially with respect to an axis of the conduit, wherein the valve comprises a blocking member positioned to block flow of the first fluid through the opening, wherein the opening moves toward an axis of the tube in response to elongation of the conduit to permit flow of the first fluid through the opening.

15. A peristaltic pump comprising:
   a monolithic conduit positioned to convey a first fluid;
   a plurality of rotor pins about which the conduit is tightly routable such that tension in the conduit causes opposing sides of the conduit to press against each other proximate each of the rotor pins to impede flow of the first fluid past the rotor pins, wherein the rotor pins are rotatable about an axis of rotation to urge the first fluid to move through the conduit; and
   a rigid plunger positioned to disengage from a rigid valve seat formed separately from the conduit to permit flow of the first fluid through the conduit in response to elongation of the conduit between the plunger and the valve seat due to impingement of the rotor pins against the conduit.

16. The peristaltic pump of claim 15, wherein the plunger moves substantially independently of a pressure gradient across the valve.

17. The peristaltic pump of claim 15, wherein plunger and valve seat are incorporated into a valve, wherein the plunger is movable with respect to the valve seat such that the plunger contacts the valve seat to impede flow of the first fluid through the conduit.

18. The peristaltic pump of claim 17, wherein the conduit comprises a tube within which the valve seat and the plunger are retained, wherein elongation of a portion of the tube between the plunger and the valve seat enables the plunger to move with respect to the valve seat.

19. The peristaltic pump of claim 18, wherein the valve seat has a generally annular shape, wherein the plunger has a sealing end and a retention end, the sealing end having a tapered shape insertable into the valve seat to substantially prevent flow of the first fluid through the valve seat, the retention end having a splined shape selected to permit passage of the first fluid between the retention end and a bore of the tube.

20. The peristaltic pump of claim 18, wherein the valve seat has a generally annular shape, wherein the plunger has a sealing end and a retention end, the sealing end having a tapered shape insertable into the valve seat to substantially prevent flow of the first fluid through the valve seat, the retention end having a plurality of passageways formed therein to permit passage of the first fluid through the retention end.

21. The peristaltic pump of claim 18, wherein the valve seat comprises a first valve seat having a generally annular shape, wherein the plunger comprises a generally spherical shape, wherein the plunger is positioned to be pressed into engagement with the first valve seat via motion of a second valve seat having a generally annular shape.

22. The peristaltic pump of claim 17, wherein the valve further comprises a rigid tubular body, wherein one of the plunger and valve seat is attached to the rigid tubular body and the other of the plunger and valve seat is attached to the conduit, wherein the rigid tubular body is resiliently coupled to the conduit to enable the plunger to move with respect to the valve seat.

23. A method for percutaneously infusing an internal wound site through the use of a system comprising a peristaltic pump having a conduit and a rotor, the method comprising:
   tightly routing the conduit about the rotor, wherein the conduit is monolithic;
   disengaging a rigid plunger from a rigid valve seat formed separately from the conduit to open the valve in response to elongation of the conduit between the plunger and the valve seat due to tight routing of the conduit about the rotor; and
   moving the rotor along the conduit to urge a first fluid to move through the conduit, toward the internal wound site.

24. The method of claim 23, wherein the system further comprises a first reservoir shaped to contain the first fluid, wherein the conduit is coupled to the first reservoir to receive the first fluid from the first reservoir, wherein urging the first fluid to move through the conduit comprises drawing the first fluid from the first reservoir.

25. The method of claim 24, wherein the system further comprises a second reservoir in communication with the internal wound site, the method further comprising receiving a second fluid aspirated from the internal wound site into the second reservoir.

26. The method of claim 23, wherein the peristaltic pump comprises multiple rotor pins, wherein tightly routing the conduit about the rotor comprises tightly routing the conduit about the plurality of rotor pins such that tension in the conduit causes opposing sides of the tube to press against each other proximate each of the rotor pins to impede flow of the first fluid past the rotor pins.

27. The method of claim 26, wherein the peristaltic pump is driven by a motor having an axis of rotation, wherein moving the rotor along the conduit comprises rotating the rotor about the axis of rotation.

28. The method of claim 23, wherein opening the valve comprises opening the valve substantially independently of a pressure gradient across the valve.

29. The method of claim 23, wherein opening the valve comprises moving the plunger with respect to the valve seat such that the plunger is withdrawn from contact with the valve seat to permit flow of the first fluid through the conduit.

30. The method of claim 29, wherein the conduit comprises a tube within which the valve seat and the plunger are retained, wherein opening the valve comprises elongating a portion of the tube between the plunger and the valve seat to enable the plunger to move with respect to the valve seat.

31. The method of claim 30, wherein the valve seat has a generally annular shape, wherein the plunger has a sealing end and a retention end, the sealing end having a tapered shape insertable into the valve seat, the retention end having a splined shape selected to permit passage of the first fluid between the retention end and a bore of the tube, wherein opening the valve comprises withdrawing the sealing end from the valve seat to permit flow of the first fluid through the valve seat.

32. The method of claim 30, wherein the valve seat has a generally annular shape, wherein the plunger has a sealing end and a retention end, the sealing end having a tapered shape insertable into the valve seat, the retention end having a plurality of passageways formed therein to permit passage of the first fluid through the retention end, wherein opening the valve comprises withdrawing the sealing end from the valve seat to permit flow of the first fluid through the valve seat.

33. The method of claim 30, wherein the valve seat comprises a first valve seat having a generally annular shape, wherein the plunger comprises a generally spherical shape, wherein opening the valve comprises withdrawing a second valve seat to permit withdrawal of the plunger from the first valve seat, wherein the second valve seat has a generally annular shape.

34. The method of claim 29, wherein the valve further comprises a rigid tubular body, wherein one of the plunger and valve seat is attached to the rigid tubular body and the other of the plunger and valve seat is attached to the conduit, wherein the rigid tubular body is resiliently coupled to the conduit, wherein opening the valve comprises moving the conduit axially with respect to the rigid tubular body to withdraw the plunger from the valve seat.

35. The method of claim 23, wherein the conduit has an opening oriented generally radially with respect to an axis of the conduit, wherein the valve comprises a blocking member positioned to block flow of the first fluid through the opening, wherein opening the valve comprises moving the opening along an axis of the tube with respect to the blocking member in response to elongation of the conduit to permit flow of the first fluid through the opening.

36. The method of claim 23, wherein the conduit has an opening oriented generally radially with respect to an axis of the conduit, wherein the valve comprises a blocking member positioned to block flow of the first fluid through the opening, wherein opening the valve comprises moving the opening toward an axis of the tube in response to elongation of the conduit to permit flow of the first fluid through the opening.

* * * * *

UNITED STATES PATENT AND TRADEMARK OFFICE
CERTIFICATE OF CORRECTION

PATENT NO. : 7,520,871 B2  
APPLICATION NO. : 10/946269  
DATED : April 21, 2009  
INVENTOR(S) : Marc Yap et al.

Page 1 of 1

It is certified that error appears in the above-identified patent and that said Letters Patent is hereby corrected as shown below:

Column 3, Line 59, ADD --(not shown)-- after "medication".

Column 4, Line 8, DELETE "us" ADD --is--.

Column 4, Line 36, DELETE the text "88" and ADD --(not visible in Fig. 3)--.

Column 5, Line 43, that portion reading "the tube 80 medication is" should read --the tube 80. Medication is--.

Column 6, Line 58, ADD --as in Figs. 2 and 3,-- after "42,".

Column 7, Line 58, DELETE the text "80" following the text "is tensioned".

Signed and Sealed this

Twenty-eighth Day of July, 2009

JOHN DOLL  
*Acting Director of the United States Patent and Trademark Office*